United States Patent [19]
Smith et al.

[11] Patent Number: 5,485,402
[45] Date of Patent: Jan. 16, 1996

[54] GAIT ACTIVITY MONITOR

[75] Inventors: Douglas G. Smith, Seattle; Aaron W. Joseph, Bellevue; David A. Boone; Robert E. Borchers, both of Seattle; Ernest M. Burgess, Mercer Island, all of Wash.

[73] Assignee: Prosthetics Research Study, Seattle, Wash.

[21] Appl. No.: 215,134

[22] Filed: Mar. 21, 1994

[51] Int. Cl.$^6$ ................................................ G01P 15/00
[52] U.S. Cl. .................. 364/566; 364/569; 340/870.01; 340/870.28
[58] Field of Search .................................. 364/566, 556, 364/565, 569; 340/870.01, 870.28

[56] References Cited

U.S. PATENT DOCUMENTS

| | | | |
|---|---|---|---|
| 3,797,010 | 3/1974 | Adler et al. | 340/323 |
| 3,972,038 | 7/1976 | Fletcher et al. | 340/189 M |
| 4,220,996 | 9/1980 | Searcy | 364/561 |
| 4,285,041 | 8/1981 | Smith | 364/415 |
| 4,371,945 | 2/1983 | Karr et al. | 364/561 |
| 4,651,446 | 3/1987 | Yukawa et al. | 36/132 |
| 4,703,445 | 10/1987 | Dassler | 364/561 |
| 4,757,453 | 7/1988 | Nasif | 364/415 |
| 4,771,394 | 9/1988 | Cavanagh | 364/561 |
| 4,774,679 | 9/1988 | Carlin | 364/550 |
| 4,855,942 | 8/1989 | Bianco | 364/561 |
| 5,130,955 | 7/1992 | Luerker et al. | 368/3 |
| 5,136,285 | 8/1992 | Okuyama | 340/870.11 |
| 5,138,550 | 8/1992 | Abraham et al. | 364/410 |
| 5,186,062 | 2/1993 | Roost | 73/865.4 |
| 5,253,654 | 10/1993 | Thomas et al. | 128/779 |
| 5,323,650 | 6/1994 | Fullen et al. | 73/172 |
| 5,369,601 | 11/1994 | Tannerbaum | 364/558 |
| 5,426,595 | 6/1995 | Picard | 364/569 |

OTHER PUBLICATIONS

Ballor et al., "Caltrac, Heart Rate and Film Estimates of Energy Expenditure Highly Correlated," *Medicine and Science in Sports and Science in Sports and Exercise* 20:2 (publication date unknown).

Doumas et al., *An Automatic Calorie Totalling Device*, Dept Electrical and Computer Engineering, University of Wisconsin–Madison, Madison, Wis. (publication date unknown).

Day, "The assessment and Description of Amputee Activity," *Prosthet. Orthot. Intl. 5:23–28, 1981*.

Holden et al., "An Assessment of a System to Monitor the Activity of Patients in a Rehabilitation Programme," *Prosthet. Orthot, Intl. 3:99–102, 1979*.

Klesges and Kesges, "The Assessment of Children's Physical Activity: A Comparison of Methods," *Medicine and Science in Sports and Exercise* 15(5):403–407, 1983.

Montoye et al., "Estimation of Energy Expenditure by a Portable Accelerometer," *Medicine and Science in Sports and Exercise* 15(5):403–407, 1983.

Sallis et al., "The Caltrac Accelerometer as a Physical Activity Monitor for School–Age Children," *Medicine and Science in Sports and Exercise* 22(5):698–703, 1990.

Smith et al., *Prosthetic History and Functional Outcome of the Isolated Traumatic Below–Knee Amputee*, manuscript in preparation accepted by the American Academy of Orthopaedic Surgeons Annual Meeting, 1993.

Washburn and Laporte, "Assessment of Walking Behavior: Effect of Speed and Monitor Position on Two Objective Physical Activity Monitors," *Research Quarterly for Exercise and Sport* 59(1):83–85, 1988.

Wong et al., "Portable Acceleraometer Device for Measuring Human Energy Expenditure." *Trans. Biomed. Eng.* 28(6):467–467–471, 1981.

*Primary Examiner*—Emanuel T. Voeltz
*Assistant Examiner*—Patrick J. Assouad
*Attorney, Agent, or Firm*—Seed and Berry

[57] ABSTRACT

A monitor records the gait activity of a wearer. The monitor is constructed to determine and record the number of steps taken by a wearer during selected intervals. The monitor includes an optical transmitter receiver to permit the monitor to be optically coupled to a stand-alone computer for transmitting data therebetween. The monitor can be programmed by the stand-alone computer to change the duration of the selected time interval period. Similarly, the gait activity data stored by the monitor can be downloaded to the stand-alone computer for analyzing the data and generating selected reports.

13 Claims, 3 Drawing Sheets

GAIT ACTIVITY MONITOR

TECHNICAL FIELD

The present invention is related to devices for recording information relating to body movements and, more particularly, a device for monitoring gait activity.

BACKGROUND OF THE INVENTION

Devices for monitoring the foot movements of athletes are known. These devices typically rely upon sensors placed on the ankle or shoe of a wearer to determine the distance covered by the wearer. Many of these devices include data transceiver devices for receiving signals from the ankle sensors and for performing rudimentary processing of these signals to provide real-time feedback to the wearer concerning stride length and/or speed.

Typical of prior art devices is that disclosed in U.S. Pat. No. 4,371,945, to Karr et al. ("the Karr et al. patent"). Therein, a pedometer is disclosed which includes first and second ultrasonic sensor modules that are strapped to the ankles of a wearer. The first and second ultrasonic sensor modules transmit signals to a processor and display module. The processor and display module are responsive to the signals received from the ultrasonic sensors for providing real-time information to the wearer concerning stride data.

However, the Karr et al. patent fails to show or suggest apparatus capable of determining and recording information relating to the gait activity of a wearer. The Karr et al. patent also does not disclose apparatus for monitoring and recording the gait activity of the wearer over prolonged periods. Further, the Karr et al. patent fails to show or suggest any ability of the disclosed pedometer for transmitting stored data to a remote system computer for data processing.

Another typical prior art device is a computer shoe system such as that disclosed in U.S. Pat. No. 4,771,394, to Cavanaugh ("the Cavanaugh patent"). Therein, a computer device is provided for coupling to a shoe and for determining when a step has been taken. The computer device includes a divider circuit for recording the number of steps taken. A cable and connector are provided for coupling the computer shoe to a system computer for providing data from the shoe computer to the system computer thereby to permit the accumulated step data to be processed.

However, the Cavanaugh patent fails to show or suggest apparatus for determining and recording selected gait activity of a wearer. Further, the Cavanaugh patent fails to disclose apparatus for transmitting stored data to a system computer without removing the computer shoe from the wearer.

Accordingly, it is desirable to provide apparatus for determining the gait activity of a wearer. It is further desirable to provide apparatus for determining the gait activity of a wearer and for recording the gait activity over an extended period of time. It is still further desirable to provide apparatus for recording the gait activity of a wearer which apparatus can provide stored information relating to gait activity to a system computer for processing.

SUMMARY OF THE INVENTION

The present invention is a monitor for recording the motion activity of a user. The monitor includes a sensor for sensing movement of the monitor relative to the environment of the wearer. The sensor is constructed to provide a movement signal indicative of the sensed movement. The monitor further includes memory for storing data related to the motion activity of the wearer. The memory is also constructed for storing a time interval data unit, wherein the time interval data unit is indicative of the length of a measurement interval. A data processor is provided and is responsive to the movement signal and the stored time interval data unit for providing a plurality of motion count data units wherein each motion count data unit is indicative of the number of movements that occur during consecutive measurement intervals. The data processor is coupled to the memory for storing the plurality of motion count data units in the memory.

In an alternative embodiment of the above described invention, a system processor is also provided for interfacing the monitor with a user to receive the plurality of motion count data units and to provide the time interval data units to the memory. Data transceivers are provided for electrically interfacing the system processor with the data processor. In still a further embodiment of the invention, the data transceivers are infrared transceiver devices for transmitting data in the form of infrared signals between the system processor and the data processor.

DETAILED DESCRIPTION OF THE INVENTION

Figure 1:
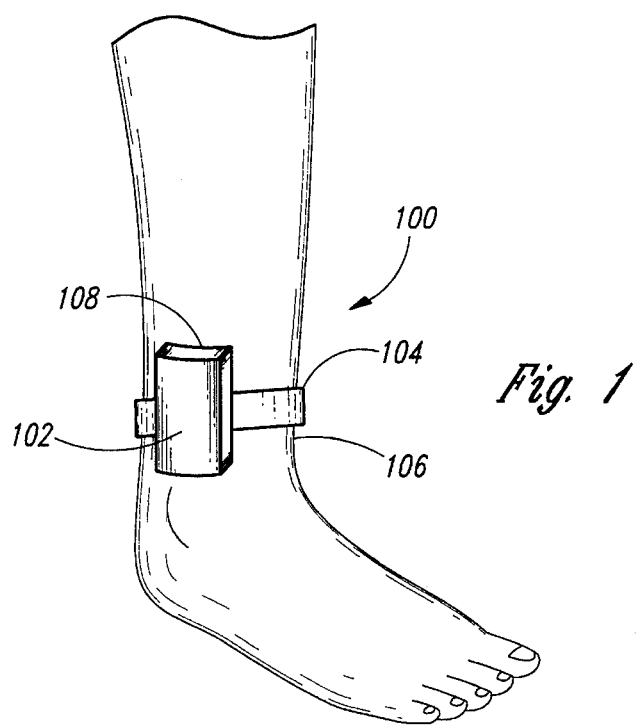
FIG. 1 is an illustration of the gait activity monitor that is the subject of the present invention, further illustrating the gait activity monitor strapped to the ankle of a wearer.

The present invention is a monitor 100, FIG. 1, for monitoring the gait activity of a wearer. As illustrated in FIG. 1, the monitor includes a housing 102 having a strap 104 fixed thereto. The strap 104 is provided for fixing the monitor 100 to the ankle 106 of a wearer. Once positioned on the wearer's ankle, the monitor 100 will record information related to the gait activity of the wearer.

Figure 4:
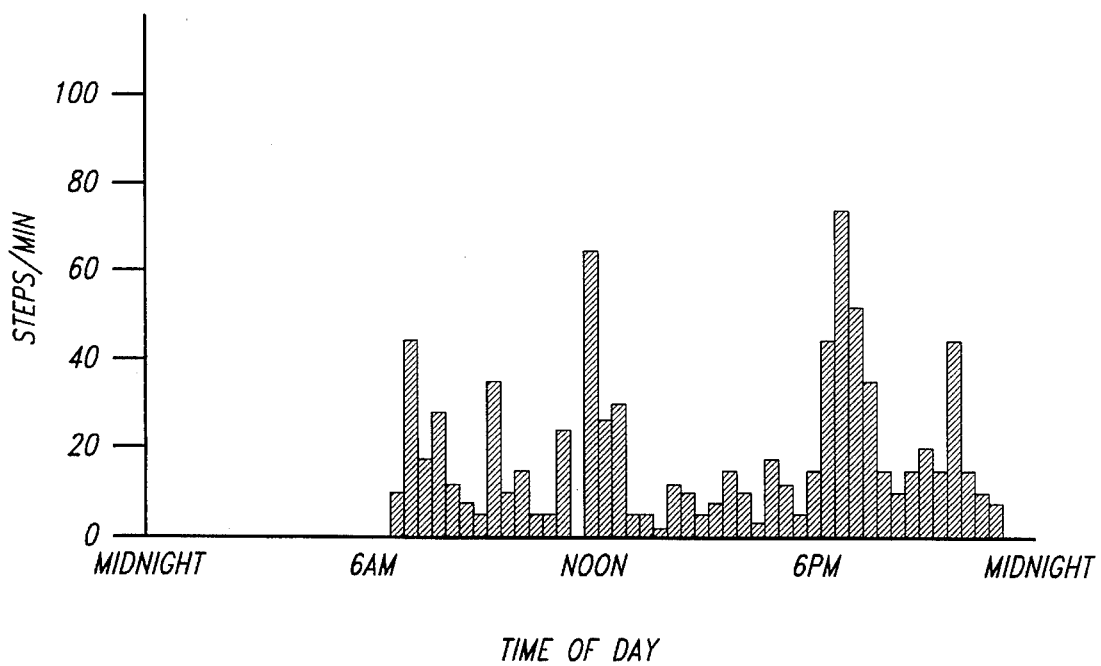
FIG. 4 is a graph of typical gait activity data provided by the gait activity monitor of FIGS. 1–3.

More particularly, the monitor 100 is constructed to record the number of steps taken by a wearer during consecutive time intervals, referred to herein as measurement time intervals. As will be described in more detail below, the monitor 100 is programmable so that a user can change the duration of the measurement time interval. Once programmed, the monitor 100 will determine when a wearer has taken a step and record the number of steps taken during each measurement time interval. The output from the monitor will be data representing the number of steps taken during each measurement time interval. FIG. 4 provides a graph illustrating the output provided by the monitor 100.

It shall be understood that although the present invention is described by reference to a monitor for recording the gait activity of a wearer, the present invention could be constructed as a monitor for recording other selected body movements of a wearer. As examples, the monitor could be constructed for recording elbow movements, shoulder movements, back movements, etc.

Referring again to FIG. 1, the housing 102 is shown to have a support surface 108 that is shaped and contoured to mate with an ankle of the wearer. However, the support surface 108 as well as other surfaces of the housing 102 can be contoured to mate with other parts of the body to permit the monitor 100 to record information relating to other body movements. In a presently preferred embodiment of the invention, the housing 102 includes a sealed internal chamber wherein the electronic portion of the monitor is mounted. Furthermore, the strap 104 may be constructed so that it can only be released by a user, who may be a therapist or other medical professional, thereby ensuring that the monitor is not removed from the ankle during a monitored time. The housing 102 is constructed to be watertight so that the wearer can wear the monitor at all times. To this end, the monitor 100 is constructed to permit a user to obtain data from the monitor without opening the housing 102. However, in alternative embodiments of the invention the housing 102 may be constructed to be opened.

Figure 2:
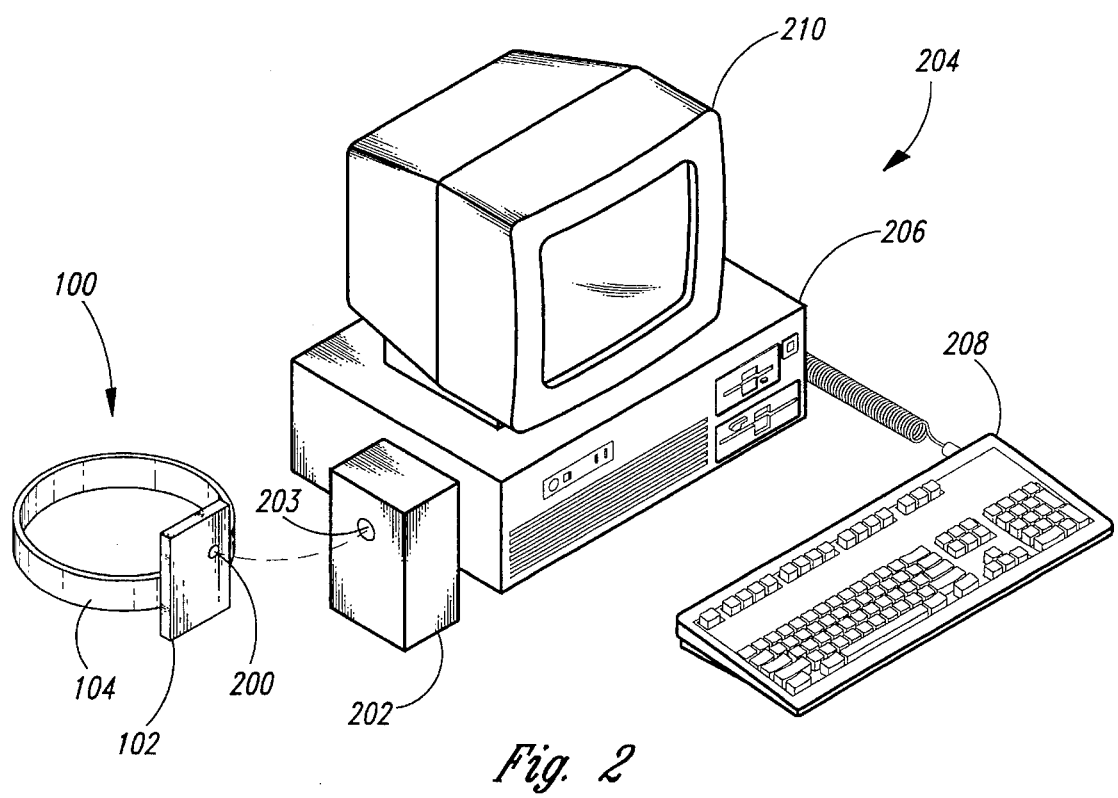
FIG. 2 is an illustration of the gait activity monitor optically coupled to a system computer using an optical datalink.
Figure 5:
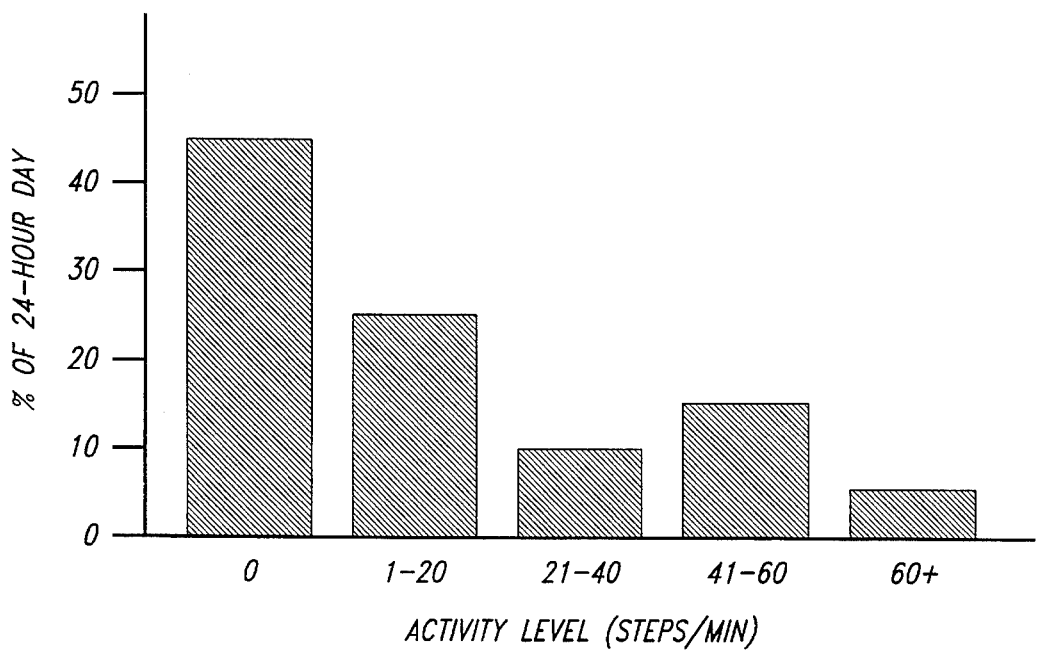
FIG. 5 is a graph illustrating data that can be obtained from the gait activity data provided by the subject gait activity monitor.

As best illustrated in FIG. 2, at least a portion of the housing 102 is constructed of a transparent material 200. As further illustrated in FIG. 2, the monitor 100 is constructed to be optically coupled to an interface module 202, via a transparent material 203, that is in turn coupled to a system processor 204. The transparent materials 200 and 203 are provided to permit transmission of optical data from the monitor 100 to the system processor 204, as will be described in greater detail below. The interface module 202 is constructed to be optically coupled to the monitor 100 to permit a user to program the monitor 100. Furthermore, the optical coupling between the monitor 100 and the interface module 202 permits a user to interrogate the monitor 100 thereby to obtain the recorded step count data. The system processor 204 is provided with programming for analyzing and reporting the step count data. As an example, the system processor 204 may be programmed to analyze the step count data and provide a report in the form as illustrated in FIG. 5.

The system processor 204 may comprise a standard personal computer having a processor portion 206 coupled to a keyboard 208 and display 210. The keyboard 208 and display 210 cooperate for interfacing a user with the processing portion 206. The interface module 202 is coupled to the processing portion 206 via an interface port (not shown) as is known in the art.

Figure 3:
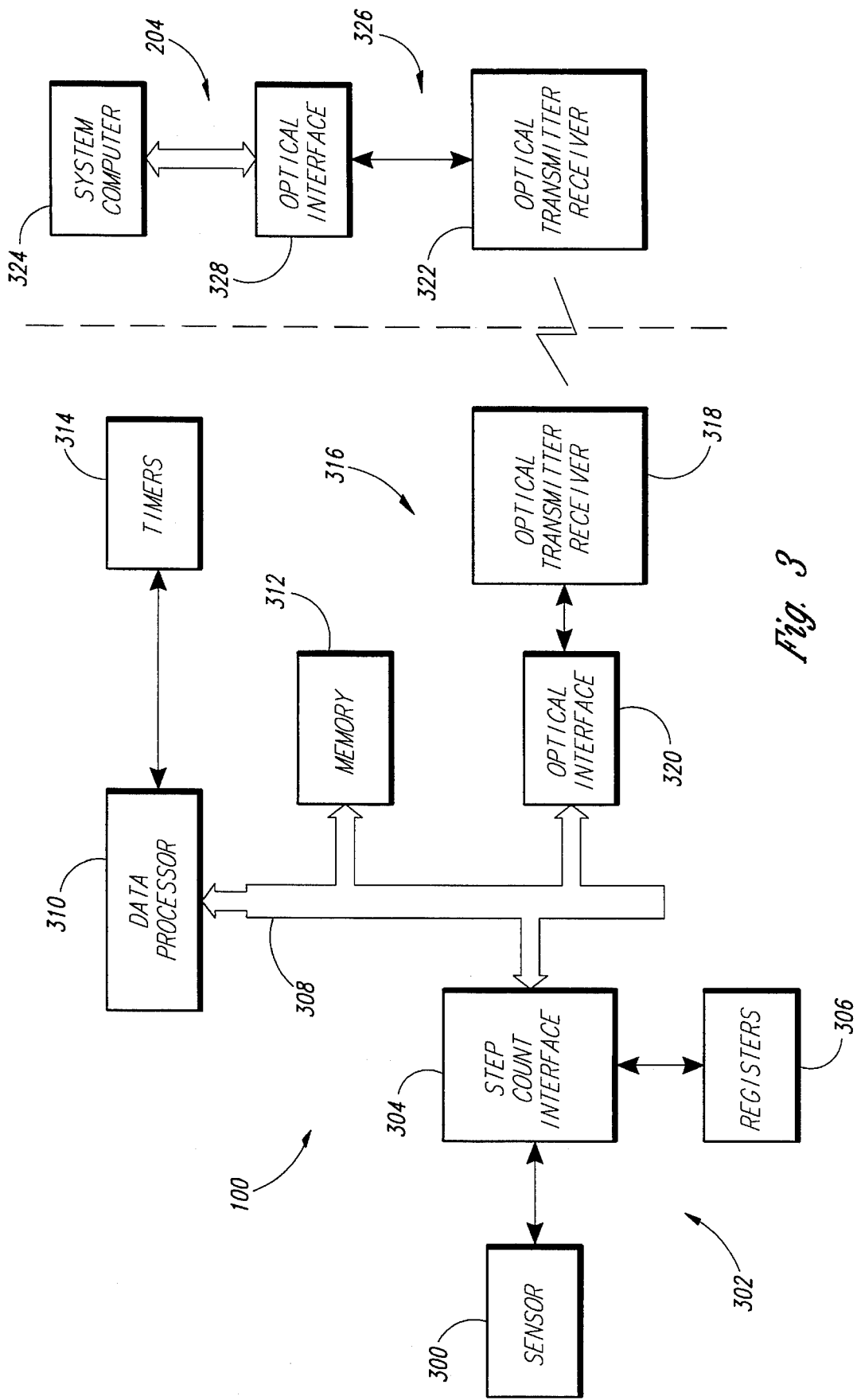
FIG. 3 is a schematic illustration of the gait activity monitor of the subject invention optically coupled to a system computer.

Referring to FIG. 3, a more detailed description of the electronics of the monitor 100 and the system processor 204 will be provided. Therein, the monitor 100 includes a sensor 300 for sensing the step motion of a user. In a presently preferred embodiment of the invention, the sensor 300 comprises an electronic accelerometer for providing an acceleration signal indicative of the acceleration of the monitor 100, which is in turn indicative of the acceleration of the ankle 106 (FIG. 1) of a wearer. In alternative embodiments of the invention, the sensor 300 may comprise single or multiple alternative sensors for sensing movement of the housing 102 relative to the environment of the housing. As examples, the sensor 300 could be constructed from a dielectric angle sensor, a mercury switch, etc. Furthermore, the sensor 300 may comprise multiple sensors for sensing movement relative to one another. Those skilled in the art will recognize that different sensors 300 may be more or less suitable for monitoring different types of movements. As an example, certain sensors may be more suitable for monitoring back movements while other sensors may be more suitable for monitoring shoulder movements.

The sensor 300 provides the acceleration signal to a step determination unit 302. The step determination unit 302 is responsive to the acceleration signal for determining whether the wearer has taken a step. The step determination unit includes a step count interface 304 coupled to one or more registers 306. The registers 306 are provided for recording step determination data such as, for example, a minimum acceleration data unit indicating a minimum acceleration required before a step will be determined, a maximum acceleration data unit indicating a maximum acceleration that will be tolerated before the acceleration signal is discounted, and a minimum time unit indicating the minimum duration that the housing must be accelerating before a step will be determined.

In a presently preferred embodiment of the invention, the registers 306 of the step determination unit 302 are programmable so that the step determination data may be changed by a user. As mentioned briefly above, and discussed in more detail below, the step determination data may be programmed by a user via the system processor 204, and the interface module 202.

The step determination unit 302 may be readily constructed from commonly available electronic components. Although the step determination unit 302 has been described herein as including registers 306 for storing the step determination data, any memory device for storing the step determination data may be used. Furthermore, details of the construction of the step determination unit will vary depending on the type of sensors 300 that are selected for the monitor 100.

The step determination unit 302 is coupled to a data bus 308 for data communication with a data processor 310. The data processor 310 is provided for determining the step activity of the wearer and for storing step count data in a memory 312. The data processor 310 may comprise any electronic circuit or circuits for performing the functions discussed herein. Similarly, the memory 312 may comprise any suitable electronic circuit or circuits for recording data as discussed herein. In a presently preferred embodiment of the invention, the data processor 310 comprises a low power microprocessor programmed to perform the function described herein. The memory 312 includes read-only memory (ROM) for storing program and instruction data for controlling the operation of the data processor 310 as is known in the art. The memory 312 also includes random access memory (RAM) for storing data for programming the data processor 310 as well as for recording data provided by the data processor 310.

Particularly, the memory 312 is constructed for storing the step count data determined by the data processor 310. The memory 312 is also constructed for storing step activity data including a time interval data unit that indicates the length of the measurement interval. The memory 312 is also constructed for storing a step rate data unit that indicates the amount of time that the step signal will be ignored after a step is counted. The step rate data unit thereby permits a user to determine a maximum gait, or step rate, that will be recorded by the monitor 100. Like the step determination data, the step activity data may be programmed by a user via system processor 204.

The data processor 310 is also coupled to timers 314. The timers 314 include a first timer for counting consecutive measurement time intervals wherein each measurement time interval is equal to the time specified by the time interval data unit stored in the memory 312. The timers 314 further include a second timer for counting a step rate time interval wherein each step rate time interval is equal to the time specified by the step rate data unit stored in the memory 312. Although the timers 314 are shown as discrete elements in FIG. 3, those skilled in the art will appreciate that the timers may actually be a portion of the data processor 310. Also, the data processor 310 may be programmed to perform the function of the timers 314.

To determine the step count data, the data processor 310 counts the number of steps taken during each step rate time interval and records this number into the memory 312. Accordingly, a new step count data unit is provided for each measurement time interval. In a presently preferred embodiment of the invention, the measurement time intervals are consecutive. However, due to the programmable nature of the monitor 100, many alternatives for specifying the measurement time interval may be provided by the user. As examples, the length of the measurement time interval may be selected. Also, the monitor 100 can be programmed to begin monitoring at a certain time and quit monitoring at a selected time. As another alternative, the monitor may be programmed to monitor a particular time period each day, e.g., 9a.m. to 11p.m. daily. As discussed above, the duration of the step rate time interval is programmable as well as the step determination data. Furthermore, the data processor 25 may be constructed for compressing the step count data before storing it in the memory 312, in accordance with compression methods known in the art. Additional data may be programmed in the memory 312, e.g., data identifying the monitor, data identifying the wearer, data identifying the programmer, etc.

The monitor 100 further includes a monitor interface 316 that is constructed from an optical transmitter/receiver 318 coupled to an optical interface 320. The optical transmitter/receiver 318 is provided for transmitting and receiving optical signals, for converting optical signals to electrical signals, and for converting electrical signals to optical signals. The optical interface 320 is constructed for coupling the electrical signals to the data bus 308 for communication with the data processor 310.

The system processor 204 includes a system computer 324 coupled to communicate with the monitor 100 via an interface module 326. The interface module is constructed from an optical transmitter/receiver 322 that is coupled to an optical interface 328. The optical interface 328 is constructed to operate in a manner similar to the optical interface 320 with the exception that the coupling between the optical interface 328 and the system computer 324 may be through a data port, as discussed above, instead of directly to a data bus.

The optical transmitter/receivers 318 and 322 may be selected from a variety of optical transducers presently available. Further, other types of transducers may be provided to couple the monitor 100 to the system processor 204. As examples, transducers for sound, electric field, or magnetic field coupling may be provided. Still further, as mentioned above, the housing 102 (FIG. 1) may be constructed to be opened to permit coupling by electric connectors.

It will be apparent to those skilled in the art that, although only several presently preferred embodiments of the invention have been described in detail herein, many modifications and variations may be provided without departing from the true scope and spirit of the invention. Accordingly, the invention is not limited except as by the appended claims.

We claim:

1. A monitor for determining the step activity of a wearer comprising:

a housing having a communication surface, said communication surface being selected of a material and opacity to permit transmission of infrared radiation, said housing having a support surface that is shaped and contoured to mate with an ankle of the wearer, said housing including a strap, fixed to the exterior of said housing, for releasably mounting the monitor to the ankle of the wearer;

an electronic accelerometer for providing an acceleration signal indicative of the acceleration of said housing;

a step determination unit coupled to receive the acceleration signal, said step determination unit including a memory device for recording a minimum acceleration data unit, a maximum acceleration data unit, and a minimum time unit, said step determination unit comparing the stored minimum acceleration data unit and the minimum time unit with the received acceleration signal for determining when the wearer of the monitor has taken a step and said step determination unit providing a step signal to indicate that the user has taken a step when the received acceleration signal is both greater than the stored minimum acceleration data unit, and less than the maximum acceleration data unit for the minimum time unit;

processor memory for storing data relating to the step activity of the wearer and for storing step activity data including a time interval data unit indicating the length of a measurement interval and a step rate data unit indicating the amount of time that the step signal will be ignored after a step is counted;

a data processor for determining the step activity of the wearer, said data processor being coupled to said step determination unit and said processor memory, said data processor including a first timer for counting consecutive measurement time intervals wherein each measurement time interval is equal to the time specified by the time interval data unit stored in said processor memory, said data processor including a second timer for counting a step rate time interval wherein each step rate time interval is equal to the time specified by the step rate data unit stored in said processor memory, said data processor being responsive to said first timer and the step signal for storing a plurality of step count data units in said processor memory wherein each step count data unit represents the number of steps made during the measurement time interval, said data processor being responsive to said second timer to count only one step during each step rate time interval;

a monitor interface, including a monitor transceiver, for transmitting and receiving infrared radiation, said monitor interface being constructed for converting received infrared radiation to electronic signals and for converting electronic signals to infrared radiation, said monitor interface being coupled to exchange electronic signals with said data processor, said electronic accelerometer, said step determination unit, said processor memory, and said data processor each being mounted in said housing with said transceiver being mounted proximate to said communication surface;

an interface module for receiving and transmitting infrared radiation to and from said monitor interface, including an interface transceiver, said interface module being constructed to convert received infrared radiation to electronic signals and to convert electronic signals to infrared radiation; and a system processor coupled to exchange electronic signals with said interface module, said system processor including a user interface and being responsive to user input for establishing communication with said data processor by way of said interface module and said monitor interface, said system processor being constructed to respond to user input to provide the time interval data unit and the step rate data unit to said data processor for storage in said processor memory, said system processor being further responsive to user input for providing the minimum acceleration data unit, and the minimum time unit to said data processor for storage in said memory device of said step determination unit, said data processor being responsive to control signals received from said system processor to provide the plurality of step count data units to said system processor.

2. A monitor for determining the step activity of a wearer comprising:

an electronic accelerometer for providing an acceleration signal having a magnitude indicative of the acceleration of an ankle of a wearer;

a step determination unit coupled to receive the acceleration signal, said step determination unit including a memory device for recording step determination data including a minimum acceptable magnitude of the acceleration signal and a minimum acceptable duration of the acceleration signal above the minimum acceptable magnitude, said step determination unit comparing the received acceleration signal with the minimum acceptable magnitude and the minimum acceptable duration and determining that the wearer of the monitor has taken a step when the magnitude of the acceleration signal is maintained for a period exceeding the minimum acceptable duration and then providing a step signal to indicate that the user has taken a step;

processor memory for storing a time interval data unit indicating the length of a measurement interval; and a data processor for determining the step activity of the wearer, said data processor being coupled to said step determination unit and said processor memory, said data processor including a step timer for counting measurement time intervals wherein each measurement time interval is equal to the time specified by the time interval data unit stored in said processor memory, said data processor being responsive to said timer and the step signal to store a plurality of step count data units in said processor memory wherein each step count data unit represents the number of steps made during the measurement time interval.

3. The monitor as recited in claim 2 wherein said processor memory is further constructed to store a step rate data unit indicating the amount of time that the step signal will be ignored after a step is counted, said data processor further comprising a second timer for counting a step rate time interval wherein each step rate time interval is equal to the time specified by the step rate data unit stored in said processor memory, said data processor being responsive to said second timer to count only one step during each step rate time interval.

4. A monitor as recited in claim 2 further comprising:

a monitor interface including a monitor transceiver for transmitting and receiving infrared radiation, said monitor interface for converting received infrared radiation to electronic signals and for converting electronic signals to infrared radiation, said monitor interface being coupled to exchange electronic signals with said data processor;

an interface module including an interface transceiver for receiving and transmitting infrared radiation to and from said monitor transceiver, said interface module being constructed to convert received infrared radiation to electronic signals and to convert electronic signals to infrared radiation; and a system processor coupled to exchange electronic signals with said interface module, said system processor including a user interface and being responsive to user input for establishing communication with said data processor by way of said interface module and said transceiver, said system processor being constructed to respond to user input to provide the time interval data unit to said data processor for storage in said processor memory, said data processor being responsive to control signals received from said system processor to provide the plurality of step count data units to said system processor.

5. A monitor for recording selected motion activity including back, arm, shoulder, hip, or leg motion of a wearer comprising:

sensor means for sensing movement of the monitor relative to the environment of the wearer, said sensor means being constructed to provide a movement signal having a magnitude for a duration that is indicative of the sensed movement;

movement selection means responsive to the movement signal for determining when the wearer of the monitor has performed a selected motion by comparing the magnitude and the duration of the movement signal with a predetermined magnitude and duration and providing a motion signal to indicate that the user has performed the selected motion when the magnitude and the duration of the movement and signal exceeds the predetermined magnitude for the predetermined duration;

processor memory means for storing a time interval data unit indicating the length of a measurement interval; and data processor means responsive to said movement selection means and said processor memory means for recording the movement activity of the wearer, said data processor means including timer means for counting measurement time intervals wherein each measurement time interval is equal to the time specified by the time interval unit stored in said processor memory means, said data processor means being responsive to said timer means and the motion signal to store a plurality of selected movement data units in said processor memory means wherein each selected movement data unit represents the number of selected movements made during the measurement time interval.

6. The monitor as recited in claim 5 wherein said processor memory is further constructed to store a motion rate data unit indicating the amount of time that the motion signal will be ignored after a selected movement is counted, said data processor means further comprising step rate timer means for counting a step rate time interval wherein each step rate time interval is equal to the time specified by the step rate data unit stored in said processor means, said data processor being responsive to said step rate timer means to count only one selected movement during each step rate time interval.

7. A monitor as recited in claim 5 further comprising:

monitor interface means for convening received infrared radiation to electronic signals and for convening electronic signals to infrared radiation, said monitor interface means being coupled to exchange electronic signals with said data processor means;

interface module means for converting infrared radiation to electronic signals and for convening electronic signals to infrared radiation; and system processor means for interfacing a user to said data processor means, said system processor means being coupled to exchange electronic signals with said interface module means, said system processor means including a user interface and being responsive to user input for establishing communication with said data processor means by way of said interface module means and said monitor interface means, said system processor means being constructed to respond to user input to provide the time interval data unit to said data processor means for storage in said processor memory means, said data processor means being responsive to control signals received from said system processor means to provide the plurality of selected movement units to said system processor.

8. The monitor as recited in claim 5 wherein said movement selection means further comprises a memory device for recording movement selection data, said movement selection means being responsive to the stored movement selection data and the movement signal for determining when the wearer of the monitor has performed the selected motion.

9. A monitor for recording motion activity including back, arm, shoulder, hip, or leg motion of a user comprising:

sensor means for sensing movement of the monitor relative to the environment of the wearer, said sensor means being constructed to provide a movement signal indicative of the sensed movement;

memory means for storing data related to the motion activity and for storing a time interval data unit indicating the length of a measurement interval;

data processing means responsive to the movement signal and the stored time interval data unit for providing a plurality of motion count data units wherein each motion count data unit is indicative of the number of movements that occur during consecutive measurement intervals, said data processing means being coupled to said memory means for storing said plurality of motion count data units in said memory means;

system processing means for interfacing said monitor with a user to receive said plurality of motion count data units and to provide said time interval data unit to said memory means; and data transceiver means for electrically interfacing said system processing means with said data processing means, wherein said data transceiver means further comprises infrared transceiver means for transmitting data in the form of infrared signals between said system processing means and said data processing means.

10. A method for monitoring the step activity of a user comprising the steps of:

(a) monitoring a signal caused by movement of the user's ankle and when the signal caused by the movement is detected, determining whether the detected movement is a step by comparing the signal's magnitude for some duration with predetermined valuer and, if the movement is not a step, continuing to monitor the user's ankle and, if the movement is a step, performing step (b);

(b) ignoring the signal caused by movement of the user's ankle for a time period indicative of a maximum step rate to be monitored and repeating step (a);

(c) repeating steps (a) and (b) for a plurality of consecutive step count intervals to determine a respective plurality of step count data units wherein each of plurality of step count data units is indicative of the total number of steps taken during the respective one of the plurality of consecutive step count intervals; and (d) storing the plurality of step count data units.

11. The method as recited in claim 10 wherein steps (a)–(d) are performed by a step count monitoring device that detects the movement and determines it is a step, said method further comprising the steps of:

(e) providing data to the step count monitoring device that is indicative of the maximum step rate and the step count interval.

12. The method as recited in claim 10 wherein steps (a)–(d) are performed by a step count monitoring device that detects the movement and determines it is a step, said method further comprising the steps of:

(f) using an infrared transmitter and receiver to provide data to the step count monitoring device that is indicative of the maximum step rate and the step count interval.

13. The method as recited in claim 10 wherein steps (a)–(d) are performed by a step count monitoring device that detects the movement and determines it is a step, said method further comprising the steps of:

(g) interfacing the step count monitoring device with a system processor by transmitting data via transceiver devices located in each of the monitoring device and the processor device; and (h) using the system processor to provide the data to the step count monitor, the data being indicative of the maximum step rate and the step count interval.

\* \* \* \* \*

UNITED STATES PATENT AND TRADEMARK OFFICE
CERTIFICATE OF CORRECTION

PATENT NO. : 5,485,402
DATED : January 16, 1996
INVENTOR(S) : Douglas G. Smith, et al.

It is certified that error appears in the above-indentified patent and that said Letters Patent is hereby corrected as shown below:

In column 6, claim 1, line 19, following "a step", please insert --,--.

In column 8, claim 7, line 64, please delete "convening" and insert therefor --converting--.

In column 8, claim 7, line 65, please delete "convening" and insert therefor --converting--.

In column 9, claim 7, line 4, please delete "convening" and insert therefor --converting--.

In column 10, claim 10, line 10, please delete "valuer" and insert therefor --values--.

In column 10, claim 10, line 19, following "each of", please insert --the--.

Signed and Sealed this

Twenty-first Day of May, 1996

Attest:

BRUCE LEHMAN

*Attesting Officer*     *Commissioner of Patents and Trademarks*